US00PP11342P

United States Patent [19]

Whitcomb

[11] Patent Number: Plant 11,342

[45] Date of Patent: Apr. 11, 2000

[54] CRAPE MYRTLE PLANT NAMED 'WHIT IV'

[76] Inventor: Carl E. Whitcomb, P.O. Box 2383, Stillwater, Okla. 74076

[21] Appl. No.: 09/027,714

[22] Filed: Feb. 20, 1998

[51] Int. Cl.[7] ..... A01H 5/00

[52] U.S. Cl. ..... Plt./252

[58] Field of Search ..... Plt./252

[56] References Cited

U.S. PATENT DOCUMENTS

P.P. 10,296 3/1998 Whitcomb ..... Plt./252

*Primary Examiner*—Howard J. Locker

*Attorney, Agent, or Firm*—Bill D. McCarthy; Phillip L. Free, Jr.; Crowe & Dunlevy, P.C.

[57] ABSTRACT

A new and distinct variety of crape myrtle, *Lagerstroemia indica*, which is characterized by a vigorous, upright growth habit; leathery leaves which emerge dark crimson and quickly change to dark green; new branches that are crimson and remain so for four or more weeks; modest seed production; inflorescences which are 12 to 20 inches tall and 8 to 12 inches wide; flower buds which are crimson before opening; and cherry red flowers that are heavily ruffled, with occasional slight variegation. The new variety is also characterized by a long bloom period.

3 Drawing Sheets

BACKGROUND OF THE INVENTION

1. Field of the Invention

The present invention relates to a new and distinct variety of cultivar of the ornamental shrub, *Lagerstroemia indica*, commonly known as crape myrtle.

2. Description of the Prior Art

The crape myrtle shrub is native to eastern China and was introduced into North America in the late 1700s. Since then, this popular ornamental shrub has been grown extensively throughout the continent. Over the years, seedlings and hybrids between *L. indica* and *L. fauriei*, have been selected for various growth forms, flower colors, or other features and propagated asexually. An assortment of methods have been utilized in attempting to develop improved varieties of crape myrtles, at least several of which have had U.S. Plant Patents issued.

For example, U.S. Plant Pat. No. 4,182, U.S. Plant Pat. No. 4,183, U.S. Plant Pat. No. 4,184, and U.S. Plant Pat. No. 4,185 disclose and claim a series of four new varieties of *Lagerstroemia indica* produced by crossing previously known varieties. Each of these new varieties was characterized as having a weeping growth habit at maturity. U.S. Plant Pat. No. 5,302 also discloses a new variety of crape myrtle exhibiting a weeping growth habit at maturity.

U.S. Plant Pat. No. 6,365 discloses a variety of crape myrtle derived from seedlings that had been treated with a mutation inducing chemical. The plant was characterized as having variegated pink flowers bordered by pure white and flowering over an extremely long period of time.

It is generally known that ethylmethane sulfonic acid methylester, EMS, is capable of producing plant mutations. EMS sometimes induces partial or complete sterility in the mutant plant and the mutants often have thicker than normal leaves and variegated flowers, with an occasional flower that is a solid color among the predominantly variegated flowers. The new variety of crape myrtle of the present invention may be such a mutant.

SUMMARY OF THE INVENTION

The present invention involves the discovery of a new and distinct variety of crape myrtle, *Lagerstroemia indica*, which has been given the cultivar name 'Whit IV' and which is characterized by a vigorous, upright growth habit, large shrub or small tree that may reach 20 feet in height. The leaves of the plant are more leathery than the species average, emerging dark crimson and quickly changing to dark green. Current seasons' stems are crimson with the color slowly diminishing with age. Inflorescences are twelve to 20 inches tall and eight to 12 inches wide. Flower buds are dark crimson. Individual petals are a guardsman to cherry red. Flowers typically open first at the base of the inflorescence and progress upward. Flower color intensity varies slightly with temperature and light: during hot summer days the flowers are more intense in color, whereas on cooler, overcast days the flower color is slightly less intense. An occasional flower may be variegated with white. Old flowers fall from the inflorescence with little discoloration. Flowering generally begins mid season relative to other crape myrtle varieties, e.g., mid July in north central Oklahoma, but flowering continues until frost. Few seeds are produced in July and August in north central Oklahoma, more seeds are produced in September and October. Flowering continues even after seed heads are produced. By contrast, many varieties of crape myrtle plants bloom heavily in July or August, set a heavy seed crop and flower sparingly, if at all, for the rest of the growing season.

DESCRIPTION OF THE VARIETY

Figure 1:
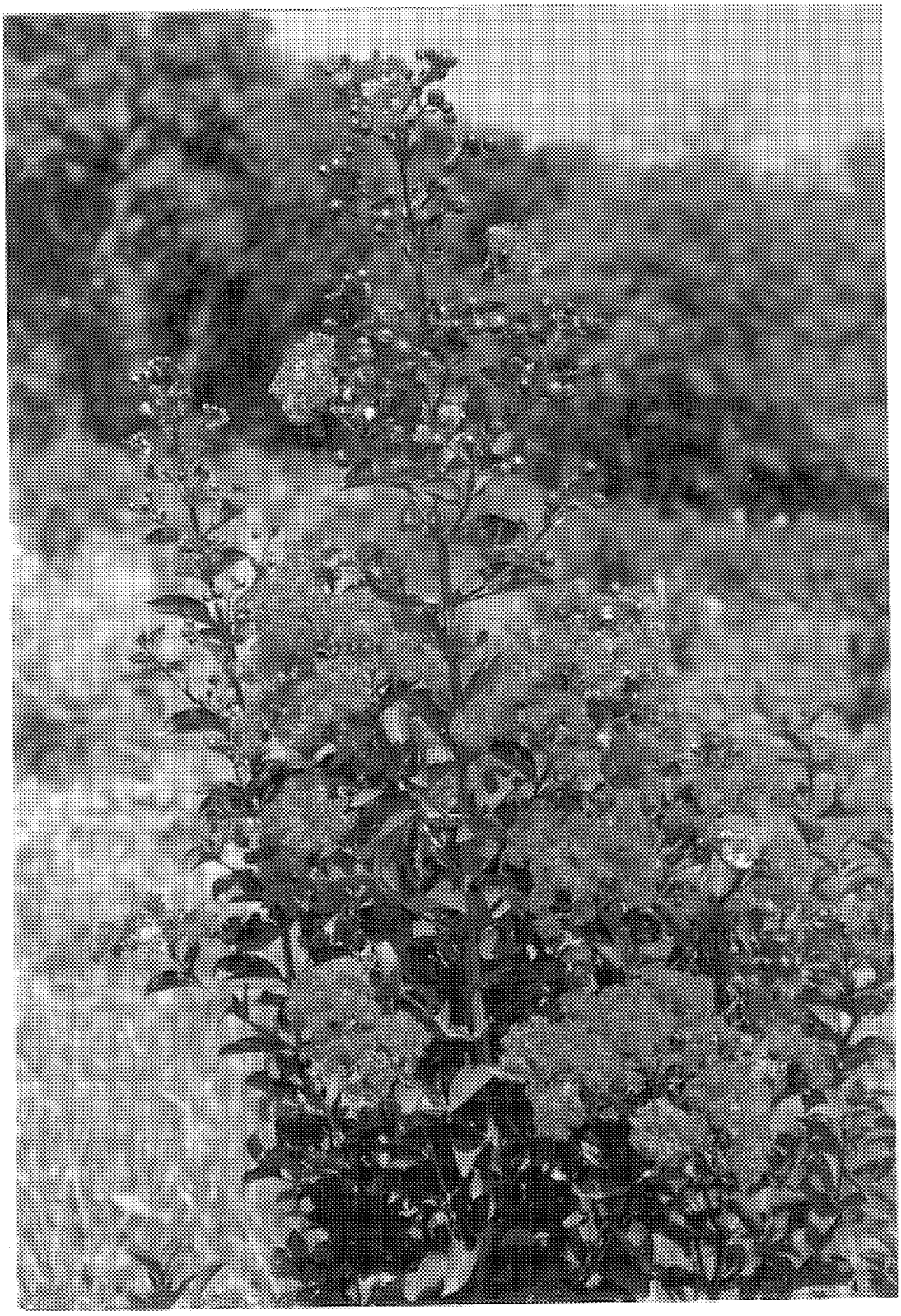
FIG. 1 is a photographic view of my new crape myrtle plant in full color showing a typical plant with upright growth and inflorescence with progressive flower opening from the base upward.

The new variety of crape myrtle, which has been give the cultivar name 'Whit IV' was selected from over 65,000 seedlings grown from an original seedling plant that had been selected because of the dark foliage and near red flowers and produced large quantities of seeds with good germination and seedling vigor. Prior to planting, the seeds were treated with ethylmethane sulfonic acid methyl ester, EMS, which is generally known to be capable of producing plant mutations. Treated seeds were planted in flats in the greenhouse. After the seeds germinated, the seedlings were transplanted into small containers and mildew was introduced from susceptible seedlings in large containers. Seedlings susceptible to mildew or with poor vigor were rogued out and the remainder of the seedlings were planted in rows in an open field for further evaluation. The new variety was selected from the population in the field for the unique foliage color, stem color, growth form, and flower color. It may be mutant seedling arising from the EMS treatment as it does have an occasional bicolor flower (see FIG. 1) and limited seed production and leathery leaves which are common among mutants.

The original asexual propagation took place in a field in north central Oklahoma from softwood cuttings. The new variety has been faithfully reproduced by such means.

Softwood cuttings taken from the original plant have been successfully rooted in a medium of peat and perlite under intermittent mist. Subsequent cuttings taken from plants resulting from previous cuttings have been similarly rooted. Growth, branching habit, flowering, and flower, foliage and branch color remain consistent with the original plant. In one test, 15 plants of the new variety, approximately 18 inches tall were planted in late July in an open field in north central Oklahoma. The plants were watered once, then evaluated for drought tolerance and the ability to establish in adverse conditions. All 15 plants survived. By contrast, other varieties of crape myrtle selections of similar age were treated similarly and most or all died.

A detailed description of the new variety of crape myrtle follows:

Parentage: Selected from over 65,000 crape myrtle seedlings grown from a selected seedling parent. The seeds were treated with EMS to induce mutations. The thick leathery leaves, occasional variegated flowers, and limited seed production are indications that the new variety may be a mutant seedling.

Growth: The plant is a vigorous grower when young. Plants from cuttings taken in June were 18 inches tall in containers when planted in the field in north central Oklahoma in October. They received no fertilizer and minimal care. One year later the plants were five feet tall and were flowering profusely. Height with age may reach 20 feet or more. Unlike some crape myrtle varieties which produce many vertical stems with moderate to vigorous side branches, this new crape myrtle plant produces a vigorous growing vertical stem with limited side branch development, thus creating an upright tree form. If the central stem is cut or killed, then a proliferation of upright stems results, but with the same vertical growth habit and limited side branch development.

Figure 2:
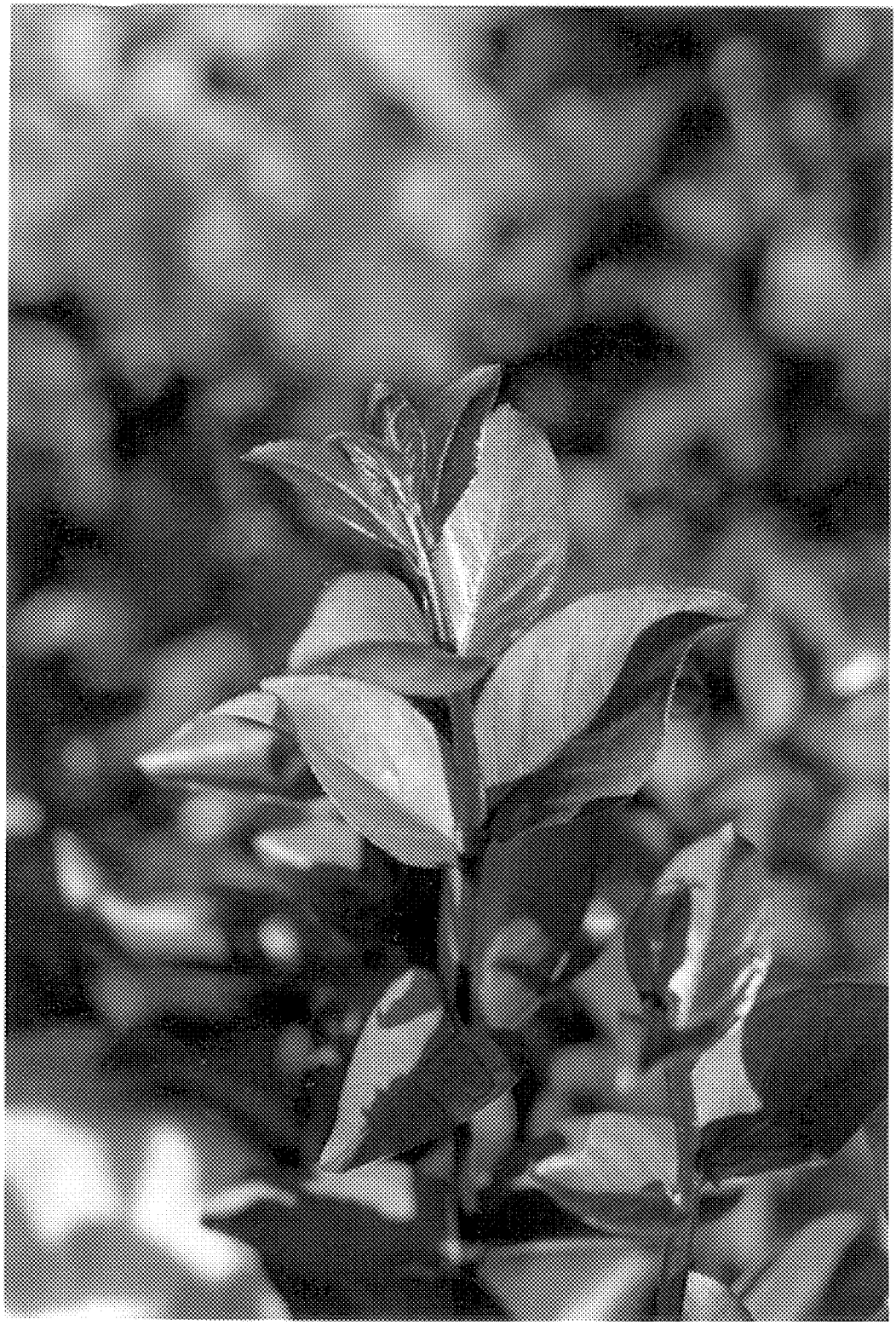
FIG. 2 is a photographic view in full color of the young branches and new and maturing foliage of the plant of FIG. 1, showing the crimson stems and new growth and the progression of color change as the leaves age and become leathery.

Branches: Young branches are crimson, grey-purple Group 187-A (R.H.S.) and CIE coordinates 0.410, 0.298, 3.4 to 187-B (R.H.S.) and CIE 0.479, 0.296, 5.1 (color notations from The Royal Horticulture Society Colour Chart, 1966 and the Commission International de l'E-clairage 1931) remaining this color for four or more weeks before gradually becoming green. The crimson young branches provide a contrast to the mature dark green leaves (FIG. 2).

Bark: The bark is typical of *Lagerstroemia indica* and is exfoliating.

Foliage: Leaves are smaller than the species average, but are more thick and leathery with excellent retention, even during severe drought. New leaves emerge crimson, grey-purple Group 187-A (R.H.S.) and CIE coordinates 0.410, 0.298, 3.4 to 187B (R.H.S.) and CIE 0.479, 0.296, 5.1 and quickly change to dark green (FIG. 2) Green Group 139-A (R.H.S.). Foliage color varies with light intensity, fertility, and growing conditions. Foliage has been very resistant to powdery mildew.

Figure 3:
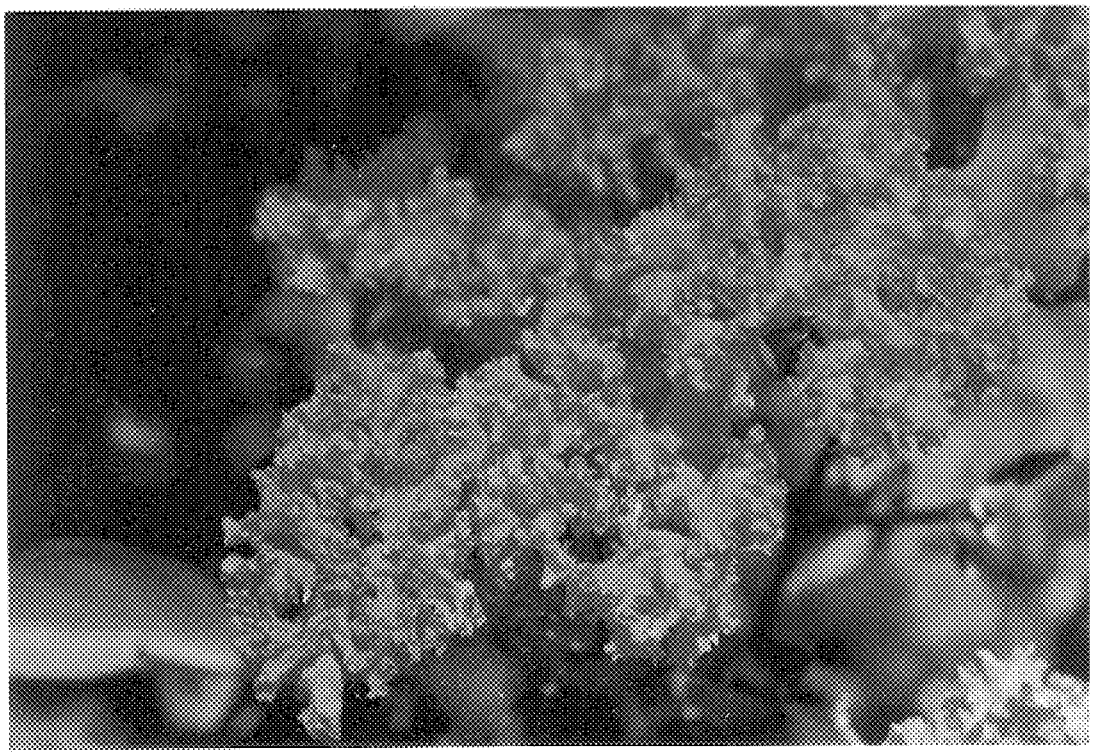
FIG. 3 is a photographic view in full color of flowers of the plant in FIG. 1 showing the heavily wrinkled petals in dense clusters that obscure the yellow stamens.
Figure 4:
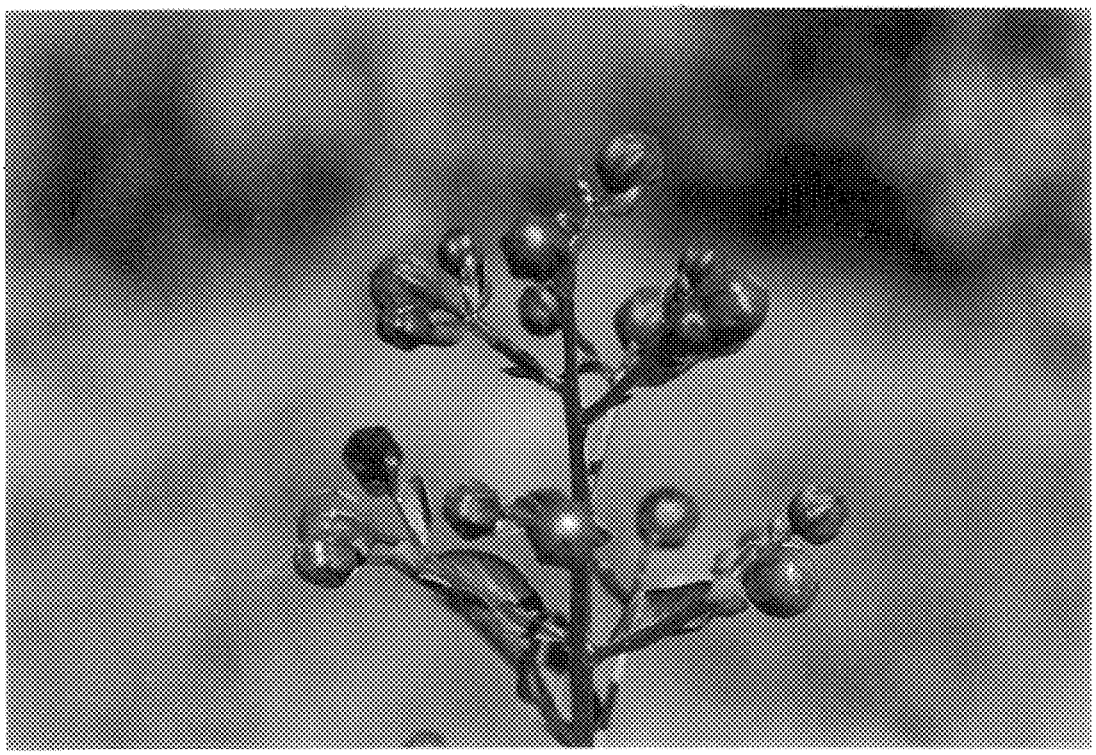
FIG. 4 is a photographic view in full color of the dark crimson flower buds on the plant in FIG. 1.

Flowers: Flower buds are crimson, grey-purple Group 187-A (R.H.S.) and CIE 0.410, 0.298, 3.4 when young, progressively becoming lighter to 187-C (R.H.S.) and CIE 0.484, 0.284, 6.1 just before opening (FIG. 4). Individual petals range from guardsman red, 45-A (R.H.S.) and CIE 0.593, 0.315, 11.9 on hot sunny days to cherry red, Red Group 45-C (R.H.S.) and CIE 0.541, 0.319, 16.3 during overcast and cooler days (FIG. 1 and FIG. 3). The presence of a flower with white margin is only occasionally expressed (FIG. 1) and varies with temperature, light intensity, and growing conditions but is generally absent. The flower petals are heavily ruffled and are generally positioned such that the stamens are obscured from view (FIG. 1 and FIG. 3). The main stem and secondary branches of the inflorescence are crimson, grey-purple Group 187-A (R.H.S.) and CIE 0.410, 0.298, 3.4 to 187-B (R.H.S.) and CIE 0.479, 0.296, 5.1 and gradually become lighter with age (FIG. 1). Flowers in an inflorescence typically open from the base, progressing upward (FIG. 1). Inflorescences are panicles and typically 12 to 20 inches tall and eight to 12 inches wide. As the flowers age they generally fall cleanly without discoloring and becoming unattractive. The plant is semi-sterile which appears to make the blooms last longer than is typical of *Lagerstroemia incida* per se. As with other crape myrtle plants, the blooms each have six petals per bloom. Bloom diameter varies with environmental conditions. Pedicel coloration is the same as the petals and the length is typical of the species. The new variety begins flowering in late July in north central Oklahoma and continues into October. Seed set is typically light in July and August and moderate in September and October in north central Oklahoma which probably extends the flowering period. Because the plant is semi-sterile, few viable seeds are produced. The viable seed pods that form are typical of the species.

Cold hardiness: The new crape myrtle has withstood temperature of −8 degrees F. in north central Oklahoma with no injury. The top of the plant was killed to the ground at −13 degrees F., but quickly regrew the following spring and flowered by late July.

Comparison to U.S. Plant Pat. No. 10,296: In comparing the presently claimed variety ("Whit IV") to that claimed in U.S. Plant Pat. No. 10,296 ("Whit II"), several differences can be noted. The Whit IV variety have flowers that are slightly lighter in color. The Whit IV flowers are 45A and 45C (R.H.S.), whereas the Whit II flowers are 46A (R.H.S.). Also, the new foliage on the Whit IV variety are distinctly crimson in color. The Whit II foliage is lighter in color, with less red pigment. Inflorescenses are distinctly larger on the Whit IV variety in that the number of flowers per inflorescences are greater than in the Whit II variety.

I claim:

1. A new and distinct variety of *Lagerstroemia indica*, crape myrtle plant substantially as shown and described and partially characterized by a vigorous upright growth habit (large shrub or small tree that may reach 20 feet or more in height), new branches that are crimson and remain so for four or more weeks, crimson new foliage that quickly changes to dark green and becomes leathery, crimson flower buds, red flowers that are heavily ruffled and in large inflorescences, modest seed production, and a long bloom period.

* * * * *

UNITED STATES PATENT AND TRADEMARK OFFICE

CERTIFICATE OF CORRECTION

PATENT NO. : PP 11,342
DATED : April 11, 2000
INVENTOR(S) : Carl E. Whitcomb

It is certified that error appears in the above-identified patent and that said Letters Patent is hereby corrected as shown below:

Column 1,
Line 33, replace "methylester" with -- methyl ester --.

Column 3,
Line 15, replace "may be mutant" with -- may be a mutant --.

Column 4,
Line 9, replace "(R.H.S.). Foliage color varies" with -- (R.H.S.) and CIE .292, .400, 6.4. Foliage color varies --.

Signed and Sealed this

Seventh Day of May, 2002

*Attest:*

*Attesting Officer*

JAMES E. ROGAN
*Director of the United States Patent and Trademark Office*